United States Patent [19]

Contractor et al.

[11] Patent Number: 5,573,992
[45] Date of Patent: Nov. 12, 1996

[54] PROCESS FOR THE CALCINATION/ACTIVATION OF V/P/O CATALYST

[75] Inventors: Rashmikant M. Contractor, Wilmington; Donald I. Garnett, Hockessin; Harold S. Horowitz, Wilmington, all of Del.; Arthur W. Sleight, Philomath, Oreg.

[73] Assignee: E. I. du Pont de Nemours and Company, Wilmington, Del.

[21] Appl. No.: 330,762

[22] Filed: Oct. 28, 1994

[51] Int. Cl.$^6$ .................................................. B01J 27/198
[52] U.S. Cl. ........................................ 502/209; 549/259
[58] Field of Search ............................. 502/209; 549/259

[56] References Cited

U.S. PATENT DOCUMENTS

| | | | |
|---|---|---|---|
| 3,864,280 | 2/1975 | Schneider | 252/435 |
| 3,915,892 | 10/1975 | Harrison | 252/435 |
| 4,111,963 | 9/1978 | Mount et al. | 549/502 |
| 4,178,298 | 12/1979 | Stefani et al. | 260/346.75 |
| 4,293,498 | 10/1981 | Lamanski et al. | 502/209 |
| 4,371,702 | 2/1983 | Bither, Jr. | 549/260 |
| 4,435,521 | 3/1984 | Yang et al. | 502/209 |
| 4,517,371 | 5/1985 | Yang et al. | 549/239 |
| 4,518,523 | 5/1985 | Blum et al. | 502/209 |
| 4,562,269 | 12/1985 | Moorehead | 502/209 |
| 4,569,925 | 2/1986 | Yang et al. | 502/209 |
| 4,668,802 | 5/1987 | Contractor | 549/259 |
| 4,677,084 | 6/1987 | Bergna | 502/8 |
| 4,748,140 | 5/1988 | Blum et al. | 502/209 |
| 5,021,588 | 6/1991 | Contractor . | |

FOREIGN PATENT DOCUMENTS 0056528  7/1982  European Pat. Off. .

*Primary Examiner*—Asok Pal

[57] ABSTRACT

An improved process for calcination and activation of a catalyst containing mixed oxides of vanadium and phosphorus (V/P/O) comprising the steps of calcining a hydrated V/P/O or V/P/O- $SiO_2$ catalyst precursor at a temperature range of 375° to 400° C. for sufficient time to dehydrate said catalyst precursor while simultaneously and continuously controlling the oxygen level such as to maintain the Vox in the range of 3.825 to 4.175; and then activating the dehydrated catalyst precursor by further heating at a range of 340° to 500° C. in the presence of a gaseous atmosphere containing n-butane at a partial pressure not exceeding 0.20 atm while simultaneously and continuously controlling the oxygen level such as to maintain the Vox in the range of 3.95 to 4.15. Such a V/P/O catalyst is useful in the preparation of maleic anhydride from n-butane.

7 Claims, No Drawings

PROCESS FOR THE CALCINATION/ACTIVATION OF V/P/O CATALYST

BACKGROUND OF THE INVENTION

1. Field of the Invention

This invention relates to an improved process for the calcination and activation of a catalyst containing mixed oxides of vanadium and phosphorus (V/P/O) useful in the preparation of maleic anhydride from n-butane.

2. Description of the Related Art

The preparation of mixed oxide compositions of vanadium and phosphorus and their use as catalysts for the oxidation of hydrocarbons to maleic anhydride is known in the art. A review of the art describing the preparation of V/P/O compositions is given in U.S. Pat. No. 4,371,702. The catalyst precursor composition is usually made by a process wherein a conventional vanadium compound in which the vanadium is in the +5 oxidation state, such as in $V_2O_5$ or $NH_4VO_3$, is partially reduced to the +4 oxidation state by reaction in either an aqueous or organic liquid medium. The catalyst precursor is then formed by the addition of any appropriate phosphorus compound, for example $H_3PO_4$, refluxing to bring about reaction and recovering the catalyst precursor, usually as a hydrated vanadium phosphate, by filtration and drying or spray drying. The prior art describes the desirable range of atomic ratios of phosphorus to vanadium and also the incorporation of catalyst promoters. It is particularly desirable that the V/P/O catalyst has good attrition resistance when it is used in a fluid bed or recirculating bed reactor. The prior art relevant to attrition resistant catalyst and its preparation is reviewed in U.S. Pat. No. 4,677,084. The production of V/P/O catalysts useful for the preparation of maleic anhydride from n-butane requires controlled calcination and activation of the catalyst precursor. This is accomplished by heating the precursor under appropriate temperature, time and atmosphere conditions to accomplish dehydration, while maintaining the average vanadium oxidation state (Vox) between specified limits. For example in U.S. Pat. No. 3,915,892 the precursor dihydrate is converted to the monohydrate by evolving one water of hydration at 370° to 394° C. while maintaining the Vox in the range of 4.1 to 4.5. The balance of the water is then removed by heating at 395° to 425° C. followed by promoting a bulk crystal phase transition above 450° C. in a carrier gas consisting of air or an inert gas together with controlled amounts of oxygen and hydrocarbon to provide an effluent stream containing at least one volume percent of oxygen or one volume percent each of oxygen and hydrocarbon, again while maintaining the Vox in the range of 4.1 to 4.5.

When the calcination/activation procedures described in the prior art are used to prepare V/P/O catalyst on the scale necessary to provide catalyst for commercial operation it is found that, from the standpoint of maleic anhydride production from n-butane, the resulting catalyst is inferior, to catalyst made on a small batch basis. Consequently more stringently controlled process conditions are needed to produce high grade catalyst on a scale required for commercial plant operation and this is now made possible by the process of this invention.

SUMMARY OF THE INVENTION

The present invention relates to a process for the preparation of a highly active and selective V/P/O catalyst capable of producing a high yield of maleic anhydride by the oxidation of n-butane. For purposes of this invention the catalyst activity is to be defined with respect to n-butane oxidation, the selectivity relates to maleic anhydride production and yield is a function of activity and selectivity. The process of this invention can be used for preparing V/P/O catalyst on any scale but it is particularly suited to the large scale production of catalyst for use in fluid bed and recirculating bed reactors associated with the commercial scale production of maleic anhydride. The procedures which have been previously described for calcination and activation have been found to give unsatisfactory catalysts when applied to large batches of precursor.

The V/P/O precursor compositions, which are converted to active catalyst by the process of this invention, can be made by any of the methods as generally known in the art such as for example the procedures described in U.S. Pat. No. 4,371,702, the teaching of which is incorporated by reference herein for such purpose. The process of this invention is also applicable to the attrition resistant V/P/O -$SiO_2$ precursor compositions such as described in U.S. Pat. No. 4,677,084, the teaching of which is also incorporated by reference herein.

The calcination and activation steps of this invention are best conducted in a fluidized bed vessel or the like. In the calcination step the precursor is brought to the temperature range of 375° to 400° C., preferably about 390° C., as quickly as possible. The oxygen level in the reactor is controlled by adjusting the proportions of air and nitrogen or of oxygen and nitrogen to maintain the Vox, which is monitored throughout, in the range of 3.825 to 4.175. A small amount of butane may also be added to the gas stream. Combustion of the butane increases the rate of heating the precursor in the fluidized bed. The temperature is then held steady until dehydration is complete maintaining the Vox between 3.825 and 4.175. Activation of the catalyst is conducted by further heating at 340° to 500° C., preferably about 460° C. for several hours. Throughout this part of the process a partial pressure of butane not exceeding 0.020 atm, preferably 0.016 atm, is maintained in the gas stream and the proportions of air and nitrogen or oxygen and nitrogen are controlled so as to maintain the continuously monitored Vox between 3.95 and 4.15. It is of critical importance to maintain the Vox between the designated limits throughout the calcination/activation process. Excursions outside these limits have an adverse effect on catalyst performance even if the final catalyst Vox is adjusted to be within the designated range. The activated catalyst is then cooled in a dry atmosphere, or it may be immediately put to use for the production of maleic anhydride from n-butane.

DESCRIPTION OF THE PREFERRED EMBODIMENTS

This invention relates to a process for the preparation of a highly active and selective V/P/O catalyst capable of producing a high yield of maleic anhydride by the oxidation of n-butane. Catalyst activity is with respect to n-butane oxidation and selectivity relates to maleic anhydride production. Yield is a function of activity and selectivity. The process of this invention can be used for preparing V/P/O catalyst on any scale but it is particularly suited to the large scale production of catalyst for use in fluid bed and recirculating bed reactors used in the commercial production of maleic anhydride. The procedures which have been previously described for calcination and activation have been found to give unsatisfactory catalyst when applied to large batches of precursor.

Thus the present invention provides an improved process for preparing a highly active and selective V/P/O catalyst comprising the steps of: (a) calcining a hydrated V/P/O or V/P/O-SiO$_2$ catalyst precursor at a temperature range of 375° to 400° C. for sufficient time to dehydrate said catalyst precursor while simultaneously and continuously controlling the oxygen level such as to maintain the Vox in the range of 3.825 to 4.175; and (b) activating the dehydrated catalyst precursor of step (a) by further heating at a range of 340° to 500° C. in the presence of a gaseous atmosphere containing n-butane at a partial pressure not exceeding 0.020 atm, preferably 0.016 atm, while simultaneously and continuously controlling the oxygen level such as to maintain the Vox in the range of 3.95 to 4.15.

It has been found that calcining in air at the much slower heating rates which occur in the case of large batches of precursor gives rise to intermediates that are over-oxidized, the Vox being greater than 4.5 in some cases. These are characterized by the appearance of VOPO$_4$ (i.e., V$^{+5}$) phases in their X-ray diffraction patterns. Subsequent reduction of the Vox back towards 4.0 and the development of single phase (VO)$_2$P$_2$O$_7$ during activation is difficult and yields catalyst characterized by inferior performance. Attempts to limit the duration of exposure of the catalyst to an oxidizing environment by carrying out a portion of the calcination heat up in nitrogen and then switching from nitrogen to air also result in inferior catalysts. In this case the catalyst first proceeds through a reduced intermediate (Vox about 3.8) as a result of the oxidation of the residual organics in the absence of molecular oxygen. Subsequent introduction of air is often characterized by a vigorous exotherm and accompanying over-oxidation. Again, relatively slow development of a single phase (VO)$_2$P$_2$O$_7$ is often observed during subsequent activation.

It has been discovered that it is important to minimize variations in Vox during both calcination and activation stages. To avoid over-oxidation or reduction during calcination the process of this invention requires that the fluidizing air be diluted with nitrogen. The nitrogen air mix that is required is dependent on the heating rate. The slower the heating rate, the longer the catalyst is exposed to oxidizing conditions, and therefor, the lower the maximum oxygen partial pressure that can be tolerated without causing over-oxidation. While oxygen partial pressure is the critical parameter, in actual practice the exit oxygen concentration of the fluidized bed is used as a controlling parameter, and the nitrogen/air mix is continuously adjusted as appropriate. A commercial scale process relies on the exothermic heat of reaction of butane for its primary source of heat. Thus, in addition to the nitrogen/air mix some amount of butane, the minimum required to maintain the desired temperature and heating rate, may be introduced during part of the calcination stage.

During the activation stage the exit oxygen concentration is similarly controlled by adjustment of the nitrogen/air mix and butane flow so as to minimize any departures in Vox outside the range of 3.95 to 4.15.

Butane partial pressure of the feed gas and/or pounds of butane fed per pound of catalyst during the activation stage are other process parameters that have been found to be highly correlated with the performance of the resulting catalyst. Lower butane levels have provided catalyst which delivers higher yields of maleic anhydride. Decreasing the partial pressure of butane to desirable levels necessitates decreasing the operating pressure of the fluid bed during activation and dilution of the butane/air flow with nitrogen.

Vanadium/Phosphorous Oxide (V/P/O) Catalyst Precursor:

V/P/O catalyst precursor compositions are made by procedures which are known to the art. The precursor compositions may incorporate catalyst promoters, components to improve attrition resistance or other beneficial components. The process of this invention is not limited to precursor compositions made by any particular method.

The catalyst precursors used in the examples of this invention were prepared by substantially following the procedures disclosed in U.S. Pat. No. 4,371,702. The use of the expression "substantially following the procedures" is not intended as an implication that the same ingredients were employed, but rather that the same general techniques were used.

(V/P/O) catalyst precursor can be made by a process in which a conventional vanadium compound wherein the vanadium is in the +5 oxidation state, such as in V$_2$O$_5$ or NH$_4$VO$_3$, is initially partially reduced to the +4 oxidation state by reaction in either an aqueous or organic liquid medium. In an aqueous medium, the reductant can comprise a soluble inorganic compound such as a halide acid (for example, concentrated hydrochloric acid), a reduced acid of phosphorus (for example, H$_3$PO$_3$), or a soluble organic compound (for example, formaldehyde, ethylene glycol, or glycolic, oxalic, citric or tartaric acid). In an organic medium, which is the preferred medium, the reductant can comprise an alcohol selected from such species as n-propyl, isopropyl, n-butyl, isobutyl, and benzyl alcohols. An organic medium is preferred since it gives higher surface area material from which a more active catalyst is subsequently obtained.

V/P/O catalyst precursor may also include a promoter which is a combination of selected materials, preferably introduced in both a specific order and chemical form, following the step in which the pentavalent vanadium compound is refluxed in an organic or aqueous medium. Suitable promoters comprise silicon and at least one of the variable valent elements selected from indium, antimony, and tantalum. In such a catalyst the Si/V atom ratio is in the range 0.02–3.0:1.0, and the (In+Sb+Ta)/V atom ratio is in the range 0.005–0.2:1.0, preferably 0.02–0.12:1.0. The P/V atom ratio is in the range 0.9–1.3:1.0.

In an aqueous system for preparing the catalyst the silicon can be introduced in the form of a colloidal silica sol; for example, as one of the Ludox® colloidal silica compositions commercially available from E. I. du Pont de Nemours and Company. In the organic system, for example in an alcoholic medium, the silicon can be added as an alkyl orthosilicate, for example tetraethyl orthosilicate. When using an orthosilicate and V$_2$O$_5$ it is preferable to add at least 0.25 mol of orthosilicate per mol of V$_2$O$_5$ following reflux of V$_2$O$_5$ in an organic or aqueous medium. The compositions which are useful in the process of the current invention have a Vox between 3.90 and 4.10.

Following reflux of a pentavalent vanadium compound in an organic or aqueous medium and optionally the introduction of the requisite promoter or promoter precursors, the catalyst precursor is formed by the addition of any commonly used appropriate phosphorus compound. For example, phosphoric acid, in such amount that the P/V atomic ratio in the ultimate catalyst is in the range 0.9–1.3:1.0. The resultant mixture is heated under reflux to give a catalyst precursor composition that can be isolated by filtration or decantation following cooling of the slurry to room temperature. This product is subsequently dried in air, inert atmosphere or vacuum at 80° to 200° C. The drying atmosphere should be such that the tetravalent state of the vanadium in the precursor is maintained.

This catalyst precursor may be formed into a convenient catalyst shape, suitable for charging to a reactor. For example by gently crushing through a 20-mesh sieve (U.S. Sieve Series), blending the resultant powder with 1–3% of a die lubricant and pellet binder, such as graphite or Sterotex®, a hydrogenated cottonseed oil commercially available from Capital City Products Co., and tableting to either ⅛" or 3/16" (3.2 or 4.8 mm) diameter pellets.

It is preferred that for use in a fluidized bed or recirculating bed reactor the catalyst have good attrition resistance. This prolongs the catalyst life requiring less replacement catalyst to be introduced to the reactor and enables the maleic anhydride production process to be operated at peak efficiency for long periods of time thus improving overall performance from an economic standpoint. The preparation of catalyst precursor from which highly attrition resistant catalyst is produced is described in U.S. Pat. No. 4,677,084. V/P/O precursor particles made as described earlier are dispersed as a slurry in an aqueous silicic acid solution equivalent to a weight of $SiO_2$ not exceeding about 6 wt %. The relative amounts of the particles and silicic acid are chosen so that the weight of the $SiO_2$ formed is about 3–15% of the total weight of the particles and the $SiO_2$. The slurry is then spray dried to form porous microspheres of attrition resistant catalyst precursor having an average particle size of 10 to 300 microns, preferably 20 to 250 microns. The porous microspheres of attrition resistant catalyst precursor are then calcined and activated by the process of the current invention. The vanadyl hydrogen phosphate precursor phase, $(VO)_2H_4P_2O_9$, (also known as the dihydrate $(VO)_2P_2O_7.2H_2O$ and perhaps more accurately as the hemihydrate $V(OH)PO_4.½H_2O$) must be converted to the catalytically active phase, $(VO)_2P_2O_7$ by calcination and activation. Besides accomplishing this structural transformation, these procedures must be carried out in such a way as to impart attrition resistance when necessary, combust residual organic matter contained in a precursor prepared in an organic medium and yield a highly active and selective catalyst.

Although the instant invention and the associated conversion of the hydrated V/P/O or V/P/O-$SiO_2$ catalyst precursor to active catalyst is being described and claimed herein with respect to simultaneous and continuous controlling of oxygen level to maintain Vox within specified ranges during calcination and activation, it should be appreciated an underlying rationale or basis founded on the nature of the phase transition can be equally presented. More specifically but without being unduly limiting in scope to any single theory or explanation, it is presently felt that the advantages and benefits of the improved process according to the present invention are related to and associated with the transformation from the $(VO)_2H_4P_2O_9$ precursor to $(VO)_2P_2O_7$ active phase being topotactic. The term topotactic refers to the fact that the morphology of the product active phase crystals remain unchanged relative to the morphology of the precursor crystals despite significant atomic-scale structural changes. It is believed that this property is responsible for maintaining the platey V/P/O morphology which provides preferential exposure of what are though to be the catalytically selective crystallographic planes. The topotactic nature of the transformation is made possible by strong structural similarities between the precursor and active phases, both of which are tetravalent with respect to vanadium. It is therefore believed important to control the vanadium state within fairly narrow limits, by adjustment of air, nitrogen and butane flows, in order to avoid the appearance of structurally unrelated phases which would prevent or inhibit the topotactic nature of the phase transformation. Thus for purposes of this invention the term "hydrated V/P/O or V/P/O-$SiO_2$ catalyst precursor" as used herein can be equally view as referring specifically to $(VO)_2H_4P_2O_9$ precursor (i.e., $(VO)_2P_2O_7.2H_2O$ and perhaps more accurately as the hemihydrate $V(OH)PO_4.½H_2O$) that under go the desired topotactic phase transition during calcination and activation.

Calcination of V/P/O Catalyst Precursor:

Catalyst precursor prepared as described above is calcined in a fluidized bed vessel. The precursor is heated to a temperature between 375° to 400° C., with about 390° C. being the optimum temperature. It is fluidized by a mixture of air and nitrogen as it is brought to the calcination temperature. When a commercial scale quantity of catalyst precursor is present in a fluidized bed the heat-up rate is slow and may take up to 20 hours or more, although it is preferred to keep the heat-up time less than about 10 hours. During heat up it is necessary to control the conditions to prevent over-oxidation or over-reduction of the vanadium component of the precursor. This can be done by adjusting the proportion of oxygen and nitrogen in the fluidizing stream so that the Vox remains between 3.825 and 4.175 at all times. The nitrogen/air mix that is required is dependent on the heating rate. The slower the heating rate, the longer the catalyst is exposed to oxidizing conditions, and therefore the lower the oxygen partial pressure that can be tolerated without causing over-oxidation. While oxygen partial pressure is the critical parameter, in actual practice the exit oxygen concentration of the fluidized bed is used as a controlling parameter and is maintained in the range of 2–4%, typically about 3%. The nitrogen/air mix fed to the vessel is continuously adjusted to keep the monitored exit oxygen at the desired level. Lower heating rates and lower organic residues in the precursor composition require lower exit oxygen levels. The heat up rate of the precursor can be increased by the addition of butane to the fluidizing gas stream, but only in amounts that are as nearly completely combusted as possible to provide additional heat. No unreacted butane should be detectable in the exit gas stream. Regardless of the specific heating rate, organic residues in the precursor charge, and the exit oxygen concentration, the objective is to maintain the catalyst Vox between 3.825 and 4.175. When the target temperature is reached it is held for about one hour to complete calcination while maintaining the same exit oxygen concentration and thereby continuing to control the vanadium oxidation state within narrow limits. If the heat-up step is very long the calcination may have been completed by the time the target temperature is reached and any further hold at this temperature may be unnecessary or only of up to a few minutes duration.

During the calcination process the precursor phase is dehydrated losing typically two moles of water, some of the organic material, if present, is combusted and a predominantly amorphous intermediate phase is formed. Frequent samples are removed from the fluidized bed during the calcination stage and they are characterized by redox titration to determine Vox and by X-ray diffraction to follow the phase changes which occur. The Vox values provide confirmation that during the entire heat-up and calcination process the vanadium oxidation state remains in the desired range. X-ray diffraction analysis monitors the conversion of precursor dihydrate to anhydrous catalyst and the development of the crystalline catalyst phase $(VO)_2P_2O_7$. These characterization procedures are used in the examples that follow.

Activation of the V/P/O Catalyst:

On completion of calcination the activation is begun. A small amount of n-butane is introduced into the fluidized gas stream and is gradually increased while controlling the oxidation state by adjusting air and nitrogen flows. For example, it has been found that controlling the exit oxygen concentration in the range of 2 to 5%, preferably 4 to 4.5%, maintains a Vox within the desired range throughout the activation step. The temperature can be within a broad range, 340° and 500° C., although it is preferred to increase the temperature to about 460° C. As the target temperature is approached the operating pressure is decreased to about 7.5 psig such that this pressure is established within an hour of reaching the target temperature. The butane partial pressure is adjusted so as not to exceed 0.020 atm, preferably 0.016 atm, to ensure that the conditions are suitable for the production of the most effective catalyst. Alternatively the butane flow should be controlled so as not to exceed 0.325 lb, preferably 0.225 lb butane fed/lb of catalyst charge. These conditions are maintained until activation is complete. At about 460° C. activation is completed in 10 to 24 hours, typically 14 to 16 hours, but longer times up to 48 hours may be necessary at lower temperature. These times are intended to give a broad indication and should not be regarded as being limiting in any way. During the activation stage samples are removed and the Vox is measured using the same method as in the calcination stage. The Vox must remain within the range 3.95 to 4.15 in order to obtain highly active and selective V/P/O catalyst. Activation is judged complete when: a)the x-ray diffraction pattern reveals single phase, crystalline $(VO)_2P_2O_7$, b) the average Vox is within the range 3.95 to 4.15, and c) stable values of butane conversion and maleic anhydride selectivity are obtained using the catalyst.

On completion of the activation stage the catalyst may be cooled to ambient temperature in a dry inert gas stream, such as nitrogen, or it may be used immediately for the production of maleic anhydride from n-butane in a recirculating solids reactor of the type described in U.S. Pat. No. 4,668,802.

Measurement of Vox:

The average oxidation number of vanadium (Vox) is determined on samples removed from the reactor by a redox titration procedure similar to that described by Nakamura et al., J. Catal. 34 (1974) 345–55. The method does not determine the relative amounts of plus 3, plus 4 and plus 5 vanadium valence states but rather the average valence or oxidation number, which is adequate for the purposes herein. About 1 gram of sample is weighed into a 125 mL Erlenmeyer flask, 10 mL of 18N $H_2SO_4$ is added and stirred at room temperature for about 15 minutes. 100 mL of a solution consisting of 40 mL 18N $H_2SO_4$ and 40 mL saturated $H_3BO_3$ diluted to 1 liter, is then added with stirring and heating at 80° C. for one hour. After cooling to room temperature a 10 mL portion of the solution is diluted to 125 mL with distilled water and all the vanadium ions are oxidized to the $V^{+5}$ state by titration with 0.1N $KMnO_4$ solution until a pink endpoint color persists for about 30 seconds. Four to six drops of an indicator solution, consisting of 0.76g barium diphenyl amine sulfonate dissolved in 100 mL 85% $H_3PO_4$, are added and the $V^{+5}$ ions are reduced to $V^{+4}$ by titration with 0.1N $Fe(NH_4)_2(SO_4)_2$ solution to a green endpoint. The average vanadium oxidation state is calculated as:

$$Vox = \frac{5.0 - mL\ KMnO_4\ solution}{mL\ Fe\ (NH_4)_2(SO_4)_2\ solution}$$

Catalyst Evaluation:

The activated catalyst is evaluated for the production of maleic anhydride by the oxidation of n-butane in a recirculating solids reactor of the type illustrated by FIG. 1 of U.S. Pat. No. 4,668,802. The catalyst is charged to the reactor fluidized bed section and heated to 380° C. while being fluidized in a gas stream having an average composition of 10% butane, 5.5% oxygen and 84.5% nitrogen. The average gas/solids contact time in the riser section reaction zone is about 1.5 seconds. The regeneration zone is also maintained at 380° C. with an air stream and an average contact time of about 7.4 minutes. After steady state conditions are established, the average maleic anhydride production rate is determined by quenching the product stream with water and titrating the recovered maleic anhydride with 0.1N NaOH solution. The average maleic anhydride production rate is expressed as grams of maleic acid carbon generated per hour (i.e., grams C/hr).

The following examples are presented to more fully demonstrate and further illustrate various individual aspects and features of the present invention while the comparative examples and showings are intended to further illustrate the differences and advantages of the present invention. As such the examples are felt to be nonlimiting and are meant to illustrate the invention but are not meant to be unduly limiting in any way particularly with respect to ultimate properties of the improved catalyst and utility of the claimed improved process.

EXAMPLE 1

This example describes the calcination and activation of a spray dried, silica-containing vanadium/phosphorus oxide catalyst precursor, $(VO)_2H_4P_2O_9$-10% $SiO_2$. The resulting attrition resistant catalyst, $(VO)_2P_2O_7$-10% $SiO_2$ was evaluated for butane oxidation in a fluid bed system for the production of maleic anhydride and gave an excellent production rate for maleic anhydride (i.e., 4.1 grams C/hr).

A fluid bed vessel approximately 21 inches in diameter was heated to 300° to 315° C. Once this temperature was established, gas flows were set at 150 lbs/hr air and 600 lbs/hr nitrogen with the system pressure controlled at 10 psig. 1600 lbs of spray dried, attrition resistant $(VO)_2H_4P_2O_9$-10% $SiO_2$ prepared by essentially the procedure of Example 1 of U.S. Pat. No. 4,677,084, omitting the addition of the catalyst promoter components $Si(OEt)_4$ and In metal, was then added to the fluid bed. After the bed level had stabilized, the air and nitrogen flows were adjusted as needed to maintain the exit oxygen concentration at 3±1% while maintaining total gas flow at 850 lbs/hr. The charge was heated as rapidly as possible maintaining the exit oxygen concentration and total gas flow specified above. Once 360° C. had been achieved (i.e., 1 hour 40 minutes after loading the catalyst) butane was added to the reactor at a low flow rate in order to increase the rate of heating. The butane flow rate was increased in small increments until 8.5 lbs/hr butane was finally achieved. The calcination temperature of 390° C. was reached 5 hours and 10 minutes after loading the catalyst and this temperature was maintained for 1 hour. During the heat-up to calcination temperature and the subsequent hold at that temperature, the 3±1% exit oxygen concentration and the 850 lbs/hr of air plus nitrogen gas flows were maintained. There was no unreacted butane detectable in the exit stream.

After the 1 hour calcination at 390° C., the air and nitrogen flows were each set to 415 lbs/hr and the butane flow was again increased in steps. During this heating ramp to activation temperature, as well as during the subsequent hold at activation conditions, the air and nitrogen flows were adjusted as necessary to control the exit oxygen concentration at 4 to 4.5% and to maintain total air plus nitrogen flow at 830 lbs/hr. Once the temperature had reached 445° C. (butane flow, 15 lbs/hr), the vessel pressure was gradually decreased so that a system pressure of 7.5 psig was established within 1 hour of having reached the activation temperature of 460° C. After having reached 460° C. (8 hours after catalyst loading), the above conditions were maintained for a duration of 14 hours. During this period the butane flow was maintained in the range of 15 to 17 lbs/hr. Average reactant flow rates during the 14 hour activation were as follows: 15.8 lbs/hr butane, 406.5 lbs/hr air and 423.2 lbs/hr nitrogen. Average reactant partial pressures during the 14 hour activation were as follows: 0.014 atm butane, 0.136 atm oxygen and 1.349 atm nitrogen. Average exit oxygen concentration during this period was 4.3% while the exit butane was always well below 500 ppm. Total pounds butane fed per pound catalyst loaded for the 14 hour activation period was 0.141. At the end of 14 hours of activation, the butane flow was stopped, the air flow replaced with dry nitrogen, the total gas flow (now all nitrogen) reduced to 755 lbs/hr and the catalyst cooled in a dry nitrogen atmosphere.

Catalyst samples were obtained frequently during the above calcination/activation process and characterized by x-ray diffraction and average vanadium oxidation state. The following table summarizes these characterizations:

| Time hrs:min | Temperature °C. | Vox | X-ray Diffraction |
| --- | --- | --- | --- |
| 00:00 | 300 | 3.95 | $(VO)_2H_4P_2O_9$ |
| 01:40 | 360 | 3.89 | $(VO)_2H_4P_2O_9$, decreasing crystallinity |
| 05:10 | 390 | 3.89 | Predom. amorphous + trace poorly crystalline $(VO)_2H_4P_2O_9$ + incipient $(VO)_2P_2O_7$ |
| 06:10 | 390 | 3.87 | Predom. amorphous + incipient $(VO)_2P_2O_7$ |
| 07:30 | 425 | 3.87 | $(VO)_2P_2O_7$, poorly crystalline |
| 07:40 | 445 | 3.97 | $(VO)_2P_2O_7$, improving crystallinity |
| 08:00 | 460 | 3.95 | " |
| 10:00 | 460 | 4.08 | " |
| 12:00 | 460 | 4.14 | " |
| 14:00 | 460 | 4.14 | " |
| 16:00 | 460 | 4.11 | " |
| 18:00 | 460 | 4.14 | $(VO)_2P_2O_7$ |
| 20:00 | 460 | 4.13 | " |
| 22:00 | 460 | 4.15 | " |

As is apparent from the preceding table, the phase transformation from precursor, $(VO)_2H_4P_2O_9$, to active phase, $(VO)_2P_2O_7$, was quite clean with no phases other than the starting and final phases resolved by x-ray diffraction. Consistent with this facile transformation were the narrow limits (3.87–4.15) within which average vanadium oxidation states were constrained. The final activated catalyst was evaluated for butane oxidation in a circulating fluid bed system. A standardized catalytic performance test was conducted using the following conditions: temperature of reaction, 380° C.; average feed composition to the riser reactor, 10% butane/ 5.5% oxygen/balance nitrogen; average gas/solids contact in riser, 1.5 sec; feed to regenerator, air; average gas/solids contact time in regenerator, 7.4 min. The average maleic anhydride production rate demonstrated by the catalyst produced in this example, when evaluated under these standardized conditions, was 4.1 grams C/hr.

Comparative Example 1

This example describes the calcination and activation of the same catalyst precursor as that used in Example 1. The Vox exceeded the upper limit in the calcination stage and the n-butane partial pressure exceeded the upper limit in the activation stage. The resulting catalyst gave an average maleic anhydride production rate which was only 51% of that given by the catalyst prepared in Example 1.

A calcination/activation was carried out in the same equipment described in Example 1 and using substantially the same catalyst precursor as described in Example 1. The system pressure was maintained at 15 psig throughout the procedure. 1900 lbs of catalyst was loaded to the fluid bed vessel pre-heated to about 300° C. Gas flows of approximately 250 lbs/hr air and 650 lbs/hr nitrogen were used as the bed temperature was increased. Once 360° C. had been achieved (i.e., 2 hours 45 minutes after loading the catalyst) butane was added to the gas stream to increase the rate of heating. The butane was increased in small increments until 25 lbs/hr of butane was finally achieved at about 400° C. along with 660 lbs/hr air and 200 lbs/hr nitrogen. This air/nitrogen mixture was maintained as the butane flow was increased to 40 lbs/hr and the temperature increased to 460° C. These activation conditions were established 9 hours after loading the catalyst, and were maintained for an additional 27 hours. During this period the reactant gas partial pressures were as follows: 0.046 atm butane, 0.285 atm oxygen and 1.689 atm nitrogen. The average exit oxygen concentration during this period was 1.75% while the exit butane was always well below 3,000 ppm. Total pounds of butane fed per pound of catalyst loaded during the 27 hour activation period was 0.465. At the end of activation, the butane flow was stopped, the air flow replaced with nitrogen and the catalyst cooled.

Catalyst samples were obtained frequently during the above calcination/activation process and characterized by x-ray diffraction and average vanadium oxidation state. The following table summarizes these characterizations:

| Time hrs:min | Temperature °C. | Vox | X-ray Diffraction |
| --- | --- | --- | --- |
| 00:00 | 300 | 4.07 | $(VO)_2H_4P_2O_9$ |
| 01:45 | 345 | 3.98 | " |
| 02:45 | 360 | 4.17 | $(VO)_2H_4P_2O_9$ decreasing crystallinity |
| 03:45 | 360 | 4.33 | Predom. amorphous + remnant $(VO)_2H_4P_2O_9$ + incipient $(VO)_2P_2O_7$ |
| 05:45 | 400 | 4.33 | Amorphous + poorly crystalline $(VO)_2P_2O_7$ |
| 06:45 | 420 | 4.44 | Amorphous + poorly crystalline $(VO)_2P_2O_7$ |
| 07:45 | 440 | 4.40 | $(VO)_2P_2O_7$, improving crystallinity + $VOPO_4$ |
| 09:45 | 460 | 4.30 | $(VO)_2P_2O_7$, improving crystallinity + $VOPO_4$ |
| 13:45 | 460 | 4.19 | $(VO)_2P_2O_7$, improved crystallinity + trace $VOPO_4$ |
| 18:00 | 460 | 4.12 | $(VO)_2P_2O_7$, improved crystallinity + trace $VOPO_4$ |
| 21:45 | 460 | 4.15 | $(VO)_2P_2O_7$ |
| 01:15 | 460 | 4.08 | " |
| 07:30 | 460 | 4.09 | " |
| 12:00 | 460 | 4.10 | " |

As is apparent from the above table and the preceeding description, this calcination/activation was conducted outside of the limits recommended in the presently disclosed invention. A standardized catalytic performance test as described in Example 1 was conducted. The average maleic anhydride production rate demonstrated by the catalyst produced in this example, when evaluated under these standardized conditions, was 2.1 grams C/hr, only about half of that obtained using the catalyst prepared in Example 1.

Comparative Example 2

This example describes the calcination and activation of the same catalyst precursor as that described in Example 1. The Vox was maintained within the limits required by the process of this invention while the n-butane partial pressure exceeded the upper limit in the activation stage. The resulting catalyst gave an average maleic anhydride production rate which was only 68% of that given by the catalyst prepared in Example 1.

A calcination/activation was carried out in the same equipment as Example 1 using substantially the same catalyst precursor as in Example 1. The system pressure was maintained at 15 psig throughout the procedure. 1,272 lbs of catalyst was loaded to the fluid bed vessel which had been pre-heated to about 300° C. Prior to loading the catalyst gas flows had been set to 150 lbs/hr air and 600 lbs/hr nitrogen. After the bed level had stabilized, the air and nitrogen flows were adjusted as needed to maintain the exit oxygen concentration at 2–3% at while maintaining total gas flow at ~850 lbs/hr. The charge was heated as rapidly as possible maintaining the exit oxygen concentration and total gas flow as specified above. Once 360° C. had been achieved (~3 hrs from loading the catalyst) butane was added to the gas stream at a low flow rate in order to increase the rate of heating. The calcination temperature of 390° C. was reached about 4 hrs from catalyst loading with a flow of about 5 lbs/hr butane. This temperature was maintained for 1 hour. During the heat-up to calcination temperature and the subsequent to hold at that temperature, the 2–3% exit oxygen concentration and the 850 lbs/hr of air plus nitrogen gas flows were maintained.

After the 1 hour calcination at 390° C., the air and gas flows were each set to 415 lbs/hr and the butane flow was again increased in steps. During this heating ramp to activation temperature, as well as during the subsequent hold at activation conditions, the air and nitrogen flows were adjusted as necessary to control the exit oxygen concentrations at 2–3% and to maintain the total air plus nitrogen flow at 830 lbs/hr. The activation temperature of 460° C. was reached with 26 lbs/hr of butane flow 8.5 hrs after loading the catalyst to the regenerator. Shortly thereafter, the butane flow was reduced to 24 lbs/hr and activation conditions were maintained with this flow for 18 hrs. Average reactant partial pressures during this 18 hr activation period were as follows: 0.03 1 atm butane, 0.227 atm oxygen and 1.763 atm nitrogen. The average exit oxygen concentration during this period was 2.08% while the exit butane was always well less than 2,000 ppm. At the end of the 18 hour activation period, the butane flow was stopped, the air flow replaced with nitrogen and the catalyst cooled.

Catalyst samples were obtained frequently during the above calcination/activation process and characterized by x-ray diffraction and average oxidation state. The following table summarizes these characterizations:

| Time hrs:min | Temperature °C. | Vox | X-ray Diffraction |
|---|---|---|---|
| 00:00 | 300 | 4.0 | $(VO)_2H_4P_2O_9$ |
| 01:30 | 340 | 3.9 | $(VO)_2H_4P_2O_9$, decreasing crystallinity |
| 02:30 | 370 | 3.92 | $(VO)_2H_4P_2O_9$, decreasing crystallinity |
| 05:30 | 390 | 3.93 | $(VO)_2H_4P_2O_9$ + $(VO)_2P_2O_7$, both very poorly crystalline + amorphous |
| 06:30 | 390 | 4.0 | $(VO)_2P_2O_7$, poorly crystalline + amorphous |
| 07:55 | 425 | 4.04 | $(VO)_2P_2O_7$, crystallinity improving |
| 08:40 | 445 | 4.03 | " |
| 10:25 | 460 | 4.06 | $(VO)_2P_2O_7$ |
| 11:15 | 460 | 4.09 | " |
| 14:15 | 460 | 4.13 | " |
| 15:15 | 460 | 4.04 | " |
| 18:15 | 460 | 4.08 | " |
| 19:15 | 460 | 4.06 | " |
| 22:15 | 460 | 4.08 | " |
| 23:30 | 460 | 4.03 | " |
| 03:30 | 460 | 4.03 | " |
| 04:30 | 460 | 4.02 | " |

As is apparent from the above table and the preceeding discussion, this calcination/activation was conducted within the limits of average vanadium oxidation state, however the butane partial pressure was above the level recommended in the present invention. A standarized catalytic performance test was conducted as described in Example 1 and Comparative Example 2. The average maleic anhydride production rate demonstrated by the catalyst produced in this example, when evaluated under these standardized conditions, was 2.8 grams C/hr., only about 68% of that obtained using the catalyst prepared in Example 1. Having thus described and exemplified the invention with a certain degree of particularity, it should be appreciated that the following claims are not to be so limited but are to be afforded a scope commensurate with the wording of each element of the claim and equivalents thereof.

We claim:

1. A process for preparing a highly active and selective V/P/O catalyst comprising the steps of:
   (a) calcining a hydrated V/P/O or V/P/O-SiO$_2$ catalyst precursor at a temperature range of 375° to 400° C. for sufficient time to dehydrate said catalyst precursor while simultaneously and continuously controlling the oxygen level such as to maintain the Vox in the range of 3.825 to 4.175; and
   (b) activating the dehydrated catalyst precursor of step (a) by further heating at a range of 340° to 500° C. in the presence of a gaseous atmosphere containing n-butane at a partial pressure not exceeding 0.020 atm while simultaneously and continuously controlling the oxygen level such as to maintain the Vox in the range of 3.95 to 4.15; thus, inducing a topotactic phase transition of $(VO)_2H_4P_2O_9$ to $(VO)_2P_2O_7$.

2. A process of claim 1 wherein the calcining and the activating are performed while the catalyst precursor is a fluidized bed.

3. A process of claim 1 further comprising the steps of cooling the resulting V/P/O catalyst in a dry atmosphere and recovering the activated catalyst.

4. A process of claim 2 wherein butane is added during calcining to increase the rate of heating of the precursor.

5. A process of claim 2 wherein said calcining is performed at about 390° C.

6. A process of claim 2 wherein activating is performed at about 460° C.

7. A process of claim 2 wherein activating is performed at a n-butane partial pressure of about 0.016 atm.

* * * * *